(12) United States Patent
von Arx et al.

(10) Patent No.: US 12,251,568 B2
(45) Date of Patent: Mar. 18, 2025

(54) POWER SOURCE FOR IMPLANTABLE MEDICAL DEVICE

(71) Applicant: BIOTRONIK SE & Co. KG, Berlin (DE)

(72) Inventors: Jeffrey A. von Arx, Lake Oswego, OR (US); Richard Berthelsdorf, Dundee, OR (US); Larry Stotts, Fulshear, TX (US)

(73) Assignee: BIOTRONIK SE & Co. KG, Berlin (DE)

( * ) Notice: Subject to any disclaimer, the term of this patent is extended or adjusted under 35 U.S.C. 154(b) by 147 days.

(21) Appl. No.: 17/211,999

(22) Filed: Mar. 25, 2021

(65) Prior Publication Data

US 2022/0305271 A1    Sep. 29, 2022

(51) Int. Cl.
*A61N 1/378* (2006.01)
*A61N 1/36* (2006.01)
*A61N 1/362* (2006.01)

(52) U.S. Cl.
CPC ......... *A61N 1/378* (2013.01); *A61N 1/36153* (2013.01); *A61N 1/36157* (2013.01); *A61N 1/362* (2013.01)

(58) Field of Classification Search
CPC .... A61N 1/378; A61N 1/3782; A61N 1/3975; A61N 1/3981
See application file for complete search history.

(56) References Cited

U.S. PATENT DOCUMENTS

| | | | | |
|---|---|---|---|---|
| 3,866,614 | A * | 2/1975 | Svensson | A61N 1/378 607/9 |
| 3,871,383 | A * | 3/1975 | Lee | H02J 9/061 320/135 |
| 6,650,942 | B2 | 11/2003 | Howard et al. | |
| 7,962,212 | B2 * | 6/2011 | Signoff | H02J 7/0024 607/34 |
| 9,421,385 | B2 * | 8/2016 | Vijayagopal | A61N 1/372 |
| 9,724,528 | B2 | 8/2017 | Boone et al. | |
| 10,431,345 | B2 * | 10/2019 | Cabauy | G21H 1/06 |
| 2010/0114215 | A1 | 5/2010 | Burnes et al. | |

OTHER PUBLICATIONS

International Search Report and Written Opinion dated Jun. 7, 2022 for International Application No. PCT/EP2022/053746, 12 pages.

* cited by examiner

*Primary Examiner* — George R Evanisko
(74) *Attorney, Agent, or Firm* — FROST BROWN TODD LLP

(57) ABSTRACT

An energy supplying component (100) includes a plurality of power sources (161, 171, 181, 191) and at least one switch (163, 165, 167, 173, 175, 177, 183, 185, 187, 193, 195, 197). Each power source of the plurality of power sources is configured to output a defined energy level. The at least one switch is configured to reversibly combine two or more power sources of the plurality of power sources for enabling the energy supplying component to supply requested energy at one or both of a needed voltage or a needed current.

9 Claims, 8 Drawing Sheets

POWER SOURCE FOR IMPLANTABLE MEDICAL DEVICE

TECHNICAL FIELD

The present invention is generally directed to an energy supplying component or battery comprising a multitude of individual power cells that may be used in the field of active implantable medical devices. The present invention is also generally directed to a method for calculating the longevity of an energy supplying component; and to a non-transitory machine-readable medium including instructions, which when executed by a machine, cause the machine to calculate the remaining longevity of an energy supplying component.

BACKGROUND

Early radioisotope cells were used in implantable medical devices (e.g., pacemakers) many years ago. One example used plutonium-238 (Pu-238) as the radioisotope (each contained 2 to 4 Ci (curies) of Pu-238). A second example used about 70 Ci of promethium-147 (Pm-147) as the radioisotope.

Newer nuclear batteries that are based on tritium (hydrogen-3) beta-voltaic cells may be safer than the older Pu-238 and Pm-147 designs, because tritium emits a beta particle with relatively benign average energy of approximately 5.7 keV; and because its decay product is a stable, non-radioactive helium isotope (helium-3). Due to the lower energy of their decay products, tritium-based beta-voltaic cells may require much less shielding than the bulky radioisotope cells of years past. While the average energy of tritium beta emission may be approximately 5.7 keV, the tritium beta emission energy may reach up to approximately 18.6 keV. Even these higher energy particles may fail to penetrate skin; and may be completely stopped by just 6 mm of air. Denser materials, such as the titanium casing of an implantable medical device, may stop these emissions in just a few tens of micrometers.

Challenges with plutonium-238 powered active implantable medical devices (AIMDs) may include toxicity of plutonium; high energy of radiation (e.g., approximately 5.6 MeV being released in its decay); relatively large and heavy devices due to shielding requirements; difficulty of procuring Pu-238; security concerns with shipping products containing plutonium; the extremely long (87.7 yr.) half-life of Pu-238; and the fact that the decay products of Pu-238 are themselves highly radioactive.

Problems with promethium-147 powered AIMDs may include the high energy of its decay (e.g., approximately 224 keV), which may cause radiation damage to an associated semiconductor; the relatively short half-life of Pm-147 (2.6 yr.) results in a relatively short lifetime (e.g., such that a commercial Pm-147 powered pacemaker may last only 7 to 9 years); relatively large and heavy devices due to shielding requirements; and the fact that the decay products of Pm-147 are themselves radioactive.

Challenges with conventionally powered implantable devices may include size and longevity. Some leadless pacemakers (alternatively called intracardiac pacemakers) and injectable monitors may have a size that is dominated by the battery. Future AIMDs may need new technologies such as tritium beta-voltaic cells for any further significant reduction in size and/or increase in longevity.

SUMMARY

It is an objective to provide AIMDs with enhanced longevity without requiring a substantial increase in size. It is also an objective to precisely and accurately predict when an AIMD will reach its end of service (EOS).

Such desires are addressed by an energy supplying component having the features of claim 1.

In one aspect, an implementation relates to an energy supplying component. The energy supplying component includes a plurality of power sources and at least one switch. Each power source of the plurality of power sources is configured to output a defined energy level. The at least one switch is configured to reversibly combine two or more power sources of the plurality of power sources for enabling the energy supplying component to supply requested energy at one or both of a needed voltage or a needed current.

In some implementations of an energy supplying component, such as that described in the preceding paragraph of this summary, the at least one switch is configured to connect individual power sources of the plurality of power sources in a serial configuration.

In some implementations of an energy supplying component, such as that described in any of the preceding paragraphs of this summary, the at least one switch is configured to connect individual power sources of the plurality of power sources in a parallel configuration.

In some implementations of an energy supplying component, such as that described in any of the preceding paragraphs of this summary, the at least one switch is configured to reversibly combine subsets of power sources of the plurality of power sources in a serial configuration.

In some implementations of an energy supplying component, such as that described in any of the preceding paragraphs of this summary, the at least one switch is configured to reversibly combine subsets of power sources of the plurality of power sources in a parallel configuration.

In some implementations of an energy supplying component, such as that described in any of the preceding paragraphs of this summary, at least one power source of the plurality of power sources comprises a beta-voltaic power source.

In some implementations of an energy supplying component, such as that described in any of the preceding paragraphs of this summary, the beta-voltaic power source including a tritium-based power source.

In some implementations of an energy supplying component, such as that described in any of the preceding paragraphs of this summary, the energy supplying component further comprises a buffer capacitor.

In some implementations of an energy supplying component, such as that described in any of the preceding paragraphs of this summary, the energy supplying component further comprises a first port and a second port. The plurality of power sources includes a first power source and a second power source. The at least one switch includes a first switch, a second switch, and a third switch. The first switch, the second switch, and the third switch are operable to selectively complete a circuit the first port to the second port. The circuit further includes one or both of the first power source or the second power source.

In some implementations of an energy supplying component, such as that described in any of the preceding paragraphs of this summary, the first switch is operable to selectively couple the first power source with the second power source in series.

In some implementations of an energy supplying component, such as that described in any of the preceding paragraphs of this summary, the second and third switches are operable to selectively couple the first power source with the second power source in parallel.

In another aspect, an active implantable medical device (AIMD) includes the energy supplying component as described in any of the preceding paragraphs of this summary.

In some implementations of an AIMD, such as that described in the preceding paragraph of this summary, the AIMD includes one or more of a pacemaker, a defibrillator, an intra-cardiac stimulation device, an implantable loop recorder, an implantable sensor, or a neuro stimulator.

In another aspect, an active implantable medical device (AIMD) includes at least one energy consuming component and at least one energy supplying component. Each of the at least one energy consuming components has an inherent energy consumption. At least one of the at least one energy supplying components is assigned to each of the at least one energy consuming components to thereby supply energy complying with the inherent energy consumption.

In some implementations of an AIMD, such as that described in any of the preceding paragraphs of this summary, each energy supplying component of the at least one energy supplying component comprising a plurality of power sources configured to output a defined energy level.

In some implementations of an AIMD, such as that described in any of the preceding paragraphs of this summary, each energy supplying component of the at least one energy supplying component comprising at least one switch configured to reversibly combine individual power sources of the plurality of power sources for supplying energy complying with one or both of voltage or current needed by the at least one energy consuming component.

In some implementations of an AIMD, such as that described in any of the preceding paragraphs of this summary, the at least one switch being configured to reversibly combine subsets of power sources of the plurality of power sources in a serial configuration or in a parallel configuration.

In some implementations of an AIMD, such as that described in any of the preceding paragraphs of this summary, the plurality of power sources comprise beta-voltaic power sources.

In some implementations of an AIMD, such as that described in any of the preceding paragraphs of this summary, the beta-voltaic power sources comprise tritium-based power sources.

In some implementations of an AIMD, such as that described in any of the preceding paragraphs of this summary, the AIMD further includes one or more of a pacemaker, a defibrillator, an intra-cardiac stimulation device, an implantable loop recorder, an implantable sensor, or a neuro stimulator.

In another aspect, a method is used to calculate the longevity of an energy supplying component. The energy supplying component comprises a multitude of individual beta-voltaic power sources outputting a defined energy level. The method comprises periodically measuring the potential of the multitude of beta-voltaic sources under a defined loading condition. The method further comprises using the measured potential to calculate the remaining longevity of the implantable system.

In some implementations of a method, such as that described in the preceding paragraph of this summary, the method further includes storing the measured potentials along with a time stamp for use in predicting remaining device longevity and in failure analysis.

In another aspect, a non-transitory machine-readable medium includes instructions. When executed by a machine, the instructions cause the machine to calculate the remaining longevity of an energy supplying component. The calculation includes measuring the potential of beta-voltaic sources under a defined loading condition. The calculation further includes performing one or both of using a look up table or solving a function. The calculation further includes obtaining the remaining longevity of the implantable system based on the measured potential and based on performing one or both of using a look up table or solving a function.

DESCRIPTION OF THE DRAWINGS

The various features and advantages of the present invention may be more readily understood with reference to the following detailed description and the embodiments shown in the drawings. Herein.

DETAILED DESCRIPTION

Figures 1, 2:
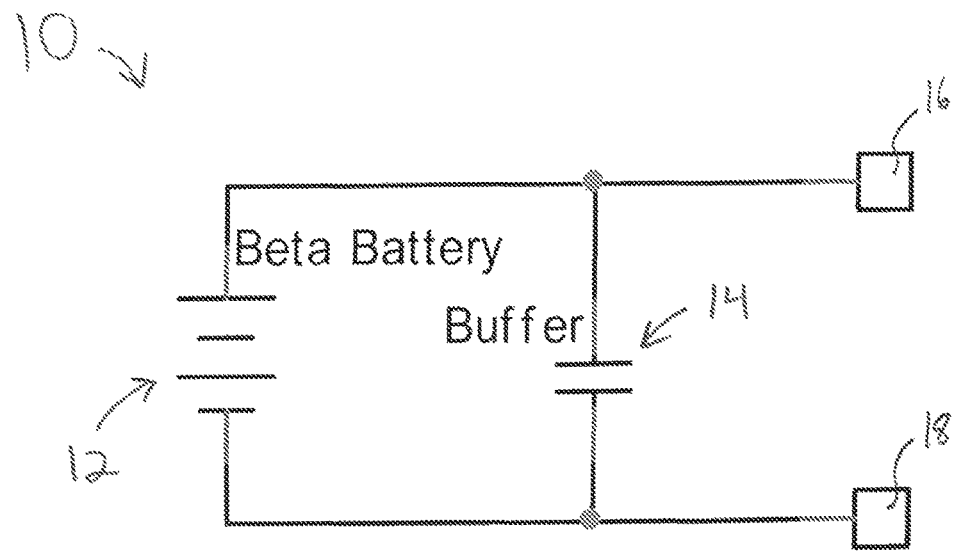
FIG. 1 shows a schematic view of a circuit including a beta-voltaic cell and a buffer capacitor.
FIG. 2 shows a schematic view of a circuit including a beta-voltaic cell and a pacing output circuit.

Subsequently, embodiments of the invention shall be described in detail with reference to the drawings. In the drawings, like reference numerals designate like structural elements.

It is to be noted that the embodiments are not limiting for the invention, but merely represent illustrative examples.

In the instant invention it is proposed to provide AIMDs with enhanced longevity without requiring a substantial increase in size. It is also proposed to provide a precise and accurate prediction of when an AIMD will reach its EOS.

Tritium beta-voltaic powered medical devices may provide significantly smaller volume and significantly higher longevity than conventional power systems. Some conventional leadless pacemakers and monitors today may be approximately 1 cc in volume. Some of these devices may use conventional lithium chemistry primary cell batteries. The battery may dominate this volume (e.g., >50% of volume). In some scenarios, the devices may last approximately 3 years (e.g., in the case of monitors) to approximately 10 years (e.g., in the case of pacemakers). It may be desirable to have an energy supplying component for AIMDs in general, particularly for miniaturized implants mentioned above, which would dramatically increase the lifetime of these implants; and at the same time fulfill the conditions of limited space usage.

To accomplish this, an energy supplying component (battery) may be formed by a multitude of individual power cells, where each of the multitude of individual power cells outputs a defined energy level. The energy level may be defined such that the energy supplying component supplies power that is minimally required for a proper function of an AIMD (or other device until the EOS.

In some versions, the energy supplying component may include at least one switch configured to reversibly combine individual power cells of the multitude of power cells, for enabling the energy supplying component to supply requested energy.

Further, an AIMD may include at least one energy consuming component and at least one energy supplying component, where each of the at least one energy consuming components has an inherent energy consumption; and where at least one of the at least one energy supplying components is assigned to each of the at least one energy consuming components, supplying energy complying with the inherent energy consumption.

A method may be used for calculating the longevity of an energy supplying component, the energy supplying component comprising a multitude of individual beta-voltaic power cells outputting a defined energy level. The method may include periodically measuring the potential of the multitude of beta-voltaic cells under a defined loading condition. The method may further include using the measured potential to calculate the remaining longevity of the implantable system.

A non-transitory machine-readable medium may include instructions, which when executed by a machine, cause the machine to calculate the remaining longevity of an energy supplying component. Such a calculation may include measuring the potential of the beta-voltaic cells under a defined loading condition, using a look up table or solving a function, in order to obtain the remaining longevity of the implantable system. A machine in this respect may be an AIMD, in particular a power management processor of an implantable medical device.

A tritium beta-voltaic cell includes a metal layer containing the tritium power source, placed near a semiconductor diode junction. Beta particles emitted by tritium decay cause electron-hole pairs in the semiconductor, which are captured in the diode junction, providing an electrical potential across the junction. The maximum voltage produced is a function of the semiconductor bandgap. The current that may be provided to an implantable medical device from the junction is a function of the beta radiation flux, the energy of the beta radiation, the efficiency of the junction at capturing the beta-voltaic energy, and the active area of the semiconductor exposed to the beta radiation flux. The beta radiation flux is itself a function of the quantity of tritium and its distribution within the metal layer, the composition of the metal layer, and time with respect to tritium's 12.3-year half-life.

Some leadless pacemakers may require power from approximately 3 μW to approximately 13 μW throughout the lifetime of the pacemaker. Some versions of individual tritium beta-voltaic cells may provide an energy density of approximately 120 nW/cm$^2$ (e.g., at the beginning of life of the cell). However, improvements in these cells may provide energy densities reaching, or exceeding, approximately 250 nW/cm$^2$ (e.g., at the beginning of life of the cell). In order to bring the relatively low voltage (e.g., approximately 0.6 V) of a single conventional cell up to a higher, more beneficial voltage (e.g., ≥3 V), several cells (e.g., six cells) may be stacked in series.

In cases where each individual cell has an active surface area of 0.22 cm$^2$ (e.g., a size consistent with the diameter of a leadless pacemaker), and assuming the requirement of either: (i) a 20 year longevity for pacing with a 1.4 V pulse amplitude and 0.24 ms pulse width, at 60 ppm into 500Ω; or (ii) a 2.5 year longevity for pacing at 3.5 V, 0.40 ms pulse width, at 60 ppm into 500Ω; then 45 6-cell clusters may be stacked in parallel to comprise a beta-voltaic energy supplying component capable of producing 3.8 μW (at 20 years) or 12.6 μW (at 2.5 years), respectively, at the end of the device's lifetime.

Substrate thinning is a well-known technology in the semiconductor industry. Thinning beta-voltaic substrates down to 10 μm total thickness may provide a 6S45P (6 series, 45 parallel) stack of 270 substrates with a total thickness of approximately 3 mm (e.g., with about 10% margin and neglecting housing thickness). By way of further example only, the 6S45P energy supplying component could equivalently be implemented either as 6 series groups of 45 parallel connected cells or as 45 paralleled groups of 6 series connected cells.

Similarly, a tritium beta-voltaic energy supplying component for an implantable monitor may utilize many stacked cell clusters to meet the power needs. However, a monitor may require less current to operate because it does not need to provide therapy such as pacing. An implantable monitor may be constructed to operate on about 5 μW average system power (including higher power communication for remote monitoring); and even less power if its sensors may be duty-cycled down to just a handful of measurements a day (e.g. applications such as implantable pressure monitoring for heart failure may require just a few measurements a day). Assuming each cell has an active surface area of 0.22 cm$^2$, then in order to achieve 2.2 μA at 2.3 V at the end of a 10-year longevity, the beta-voltaic energy supplying component for a monitor may be, for example, 4S45P, with a total of 180 stacked cells. The stack height for such an energy supplying component may be approximately 2 mm (with the same assumptions as before).

As noted above, tritium beta-voltaic power supplies for implantable medical devices may provide relatively smaller size and/or longer longevity as compared to implantable medical devices using other kinds of power supplies. In addition, tritium-based beta-voltaic cells in implants may allow for several degrees of freedom that are not readily accessible with chemical batteries.

Given a tritium-based beta-voltaic powered implant with the requirement that it must provide paces (or some other therapy, or monitoring) needing maximum power P at T=time of EOS in years, then its energy source must be sized to provide potential power $P*2^T/12.3$ at the beginning of service (BOS). That is, at any time t from t=0 at BOS until t=T at EOS there will be an excess power available equal to the following:

$$P*(2^{T}/12.3 - 2^{t}/12.3)$$

In some cases, there may be no downside to using that excess power at any time, even continuously. This may contrast with a device powered by a chemical cell, which may have a fixed capacity so that the faster stored energy is used (e.g., the higher the power delivered), the sooner the chemical cell is depleted. The excess power in a tritium-based beta-voltaic power supply may be used for functionality that is desirable to have for some initial portion of the device's service time; and acceptable to not have in the later portion. For example, it may be acceptable to have capture recognition and/or frequent communication available only in the early stages of an implant.

FIG. 1 shows a basic circuit 10 comprising a beta-voltaic power source 12 and a buffer capacitor 14, with ports 16, 18 for drawing power from the circuit 10. As used herein, the term "beta-voltaic power source" should be read to include power sources that comprise one or more beta-voltaic cells. If a circuit element requires pulsed power (e.g., for pacing or communication), it may draw it from a storage capacitor that is directly connected to a beta energy supplying component that provides at least the average power required. There does not necessarily need to be any isolation or resistance between the energy supplying component and capacitor. Given time, the beta-voltaic power source 12 may charge the buffer capacitor 14 up to the limit of its open circuit voltage (subject, of course, to leakage of the capacitor 14).

FIG. 2 depicts an example of a pacing circuit 20 for a leadless pacemaker that includes a beta-voltaic power source 22, a reservoir capacitor 24, a pair of switches 30, 32, a series pace capacitor 34, and a pair of pacing electrodes 36, 38. By way of example only, pacing electrode 36 (cathode) and pacing electrode 38 (anode) may be configured as direct connections to a leadless pacemaker. Alternatively, this configuration could also be formed by a traditional pacemaker, where cathodic pacing electrodes 36 are provided on a cardiac lead connected to a traditional subcutaneously implanted pacemaker having a case used as anodic electrode 38. The circuit of FIG. 2 may be unsuitable for use with a power source capable of sourcing currents greater than those desired for a stimulus pulse.

The voltage produced by a beta-voltaic cell is dependent on its semiconductor material and structure, as well as on the current that it supplies. Thus, where examples of 0.4 and 0.6 V are given herein, that may be different for different materials and/or loads.

Since a beta-voltaic cell may be incapable of delivering more than a fixed, generally small, current, there may be no need to mitigate the hazard of a beta-voltaic cell being short circuited (other than, e.g., the hazard of loss of functionality due to power loss). Conversely, short-circuiting a beta-voltaic cell will not necessarily damage the beta-voltaic cell or reduce the future capacity of the beta-voltaic cell.

A beta-voltaic energy supplying component may be configured to meet the specific needs of a circuit element. For example, consider a device that incorporates a control block requiring 1.2 V at 1.0 µA; and an active component (e.g., electrical stimulus feature, sensor, a combination of those, and/or other kind(s) of active component(s)) requiring 4.0 V at an average of 3 µA. This may be powered by two dedicated beta-voltaic energy supplying components, each made up of a multiplicity of cells that each provide 0.4 V at 100 nA. One dedicated beta-voltaic energy supplying component for the control block may include 10 paralleled groups of 3 cells in series (3S10P). One dedicated beta-voltaic energy supplying component for the active component may include 30 paralleled groups of 10 cells in series (10S30P). This is shown in the circuit 40 of FIG. 3, where a dedicated stimulus energy supplying component 42 is interposed between an active component port 46 and a ground port 50; and a dedicated control energy supplying component 44 is interposed between a control block port 48 and the ground port. In some scenarios, this arrangement of circuit 40 may eliminate losses associated with voltage conversion. Also in some scenarios, circuit 40 may include more than one active component, where at least one of the active components requires a voltage and/or current draw that differs from the voltage and/or current draw required by one or more of the other active components.

Figure 3:
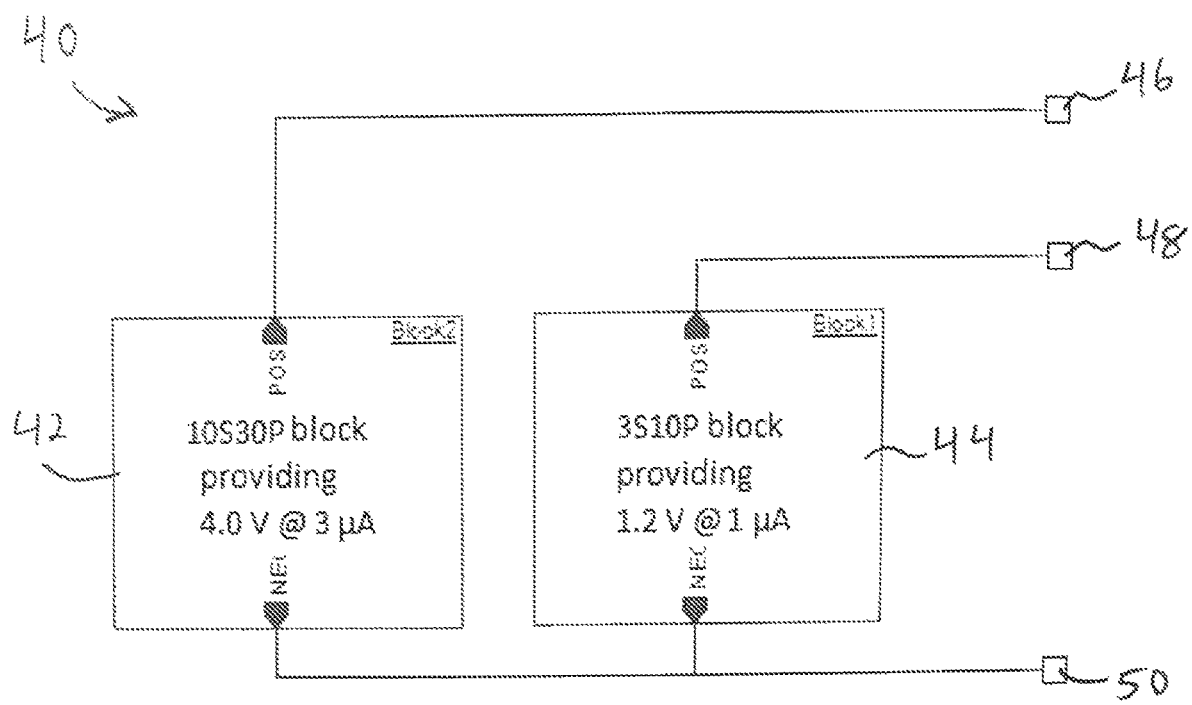
FIG. 3 shows a schematic view of a circuit including two differently-sized beta-voltaic energy supplying components in a first arrangement.
Figure 4:
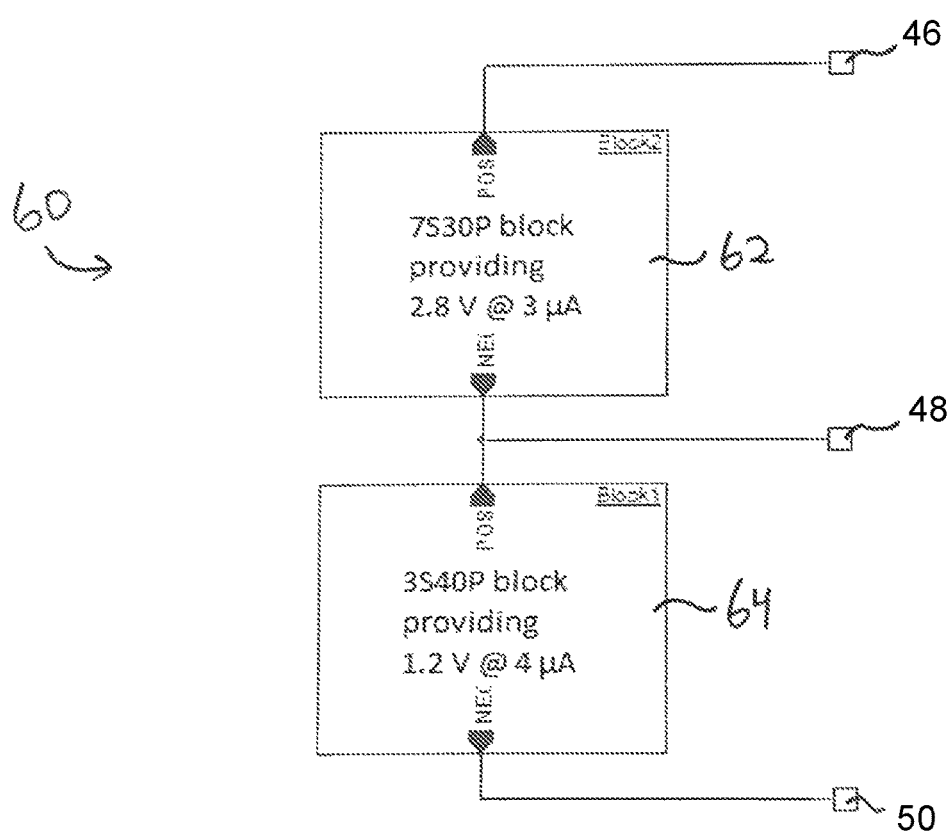
FIG. 4 shows a schematic view of a circuit including two differently-sized beta-voltaic energy supplying components in a second arrangement.

Rather than using independent blocks of cells for powering different circuit elements, asymmetric configurations could also be used. FIG. 4 shows a circuit 60 where two differently-sized beta-voltaic energy supplying components 62, 64 could be used to power the same hypothetical circuit as in FIG. 3 above, via corresponding ports 46, 48, 50. The same total number of cells (10×30+3×10=7×30+3×40=330) may be used in either circuit 40 or 60. One advantage that circuit 60 may have over circuit 40 is that circuit 60 may minimize the number of interconnections to the energy supplying component. Another advantage circuit 60 may offer over circuit 40 is that circuit 60 may provide the possibility of powering the circuit element that requires only 1.2 V at 1 µA for a longer time than originally planned for, if the circuit element requiring 4 V at 3 µA is not needed to draw power simultaneously. As with circuit 40, circuit 60 may include more than one active component, where at least one of the active components requires a voltage and/or current draw that differs from the voltage and/or current draw required by one or more of the other active components.

An advantage of the arrangement using distinct energy supplying components, as provided in circuit 40, is that it decouples the two power supplies 42, 44 relative to each other. In the example of FIG. 4, if the circuit requiring 1.2 V ever draws more than its original allotment, the element requiring 4 V at 3 µA may be adversely affected; but if the configuration of FIG. 3 is followed, there may be no interaction through the energy supplying components 42, 44.

Figure 5A:
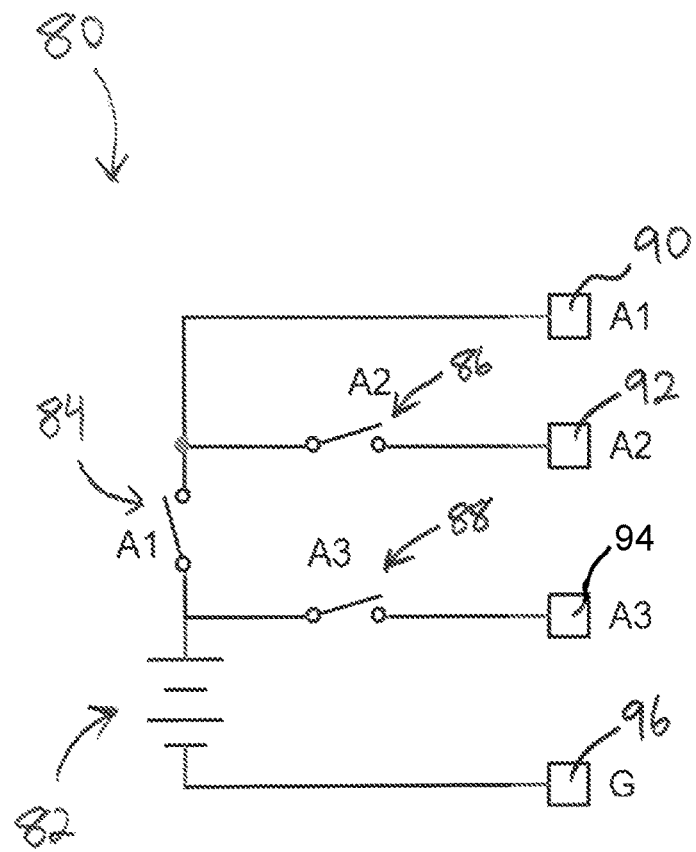
FIG. 5A shows a schematic view of an energy supplying circuit module, with components of module illustrated separately.
Figure 5B:
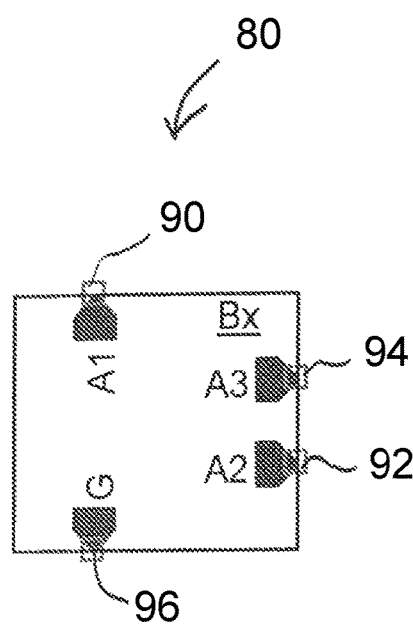
FIG. 5B shows a schematic view of the module of FIG. 5A, in block form.

As shown in FIGS. 5A-5B, energy supplying components may be made in modules 80. FIG. 5A shows the components of the module 80 including a beta-voltaic power source 82, a set of switches 84, 86, 88, and a set of ports 90, 92, 94, 96. Port 90 is associated with switch 84, such that switch 84 is interposed between beta-voltaic power source 82 and port 90. Port 92 is associated with switch 86, with switch 86 being interposed between switch 84 and port 92; and with switch 84 being interposed between switch 86 and beta-voltaic power source 82. Port 94 is associated with switch 88, such that switch 88 is interposed between beta-voltaic power source 82 and port 90. Port 96 is configured to couple with ground. FIG. 5B shows how module 80 may be represented in block form.

Figure 6:
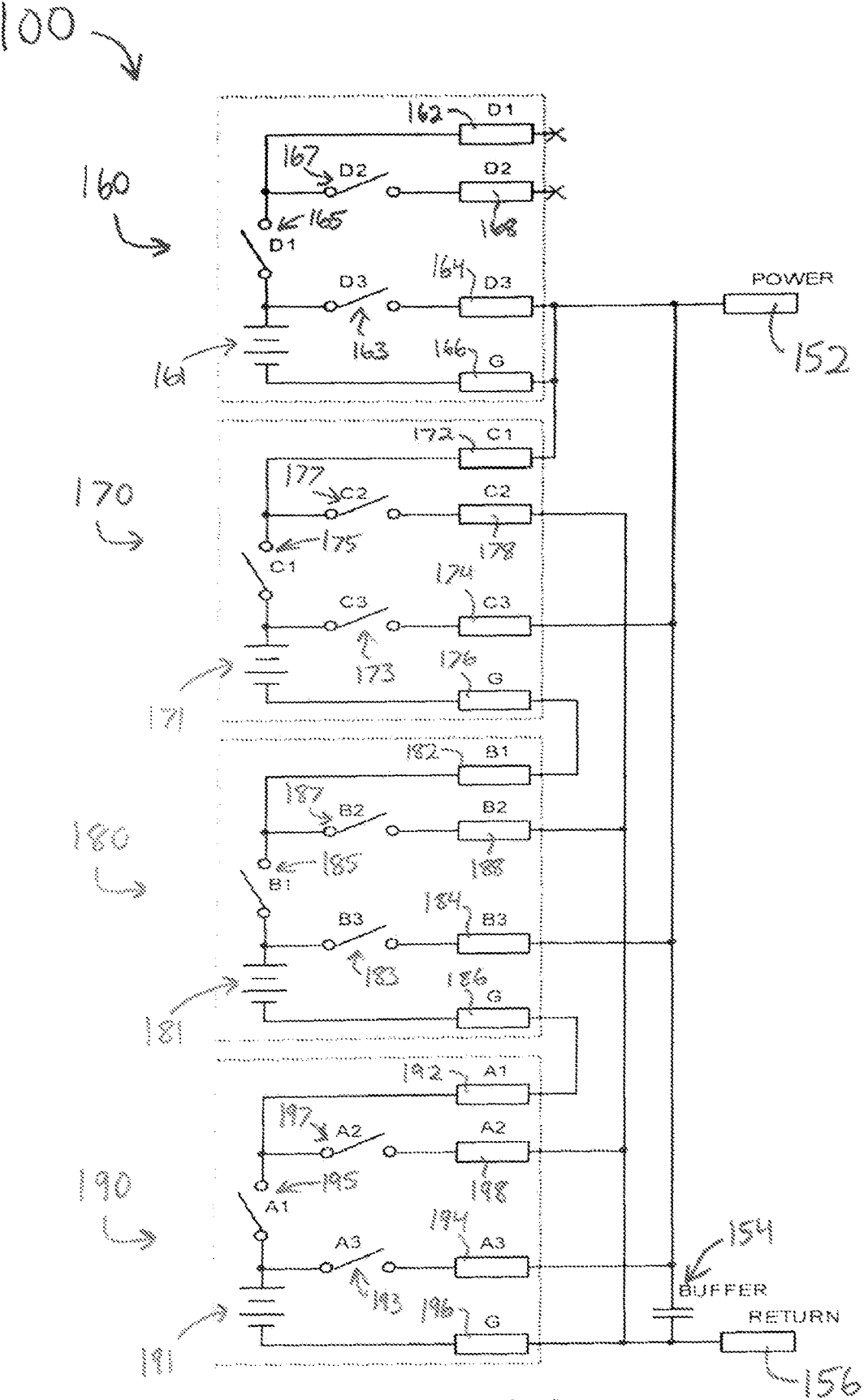
FIG. 6 shows a schematic view of a circuit of an energy supplying module formed by four beta-voltaic power sources that may be connected in various parallel/serial configurations.
Figure 7:
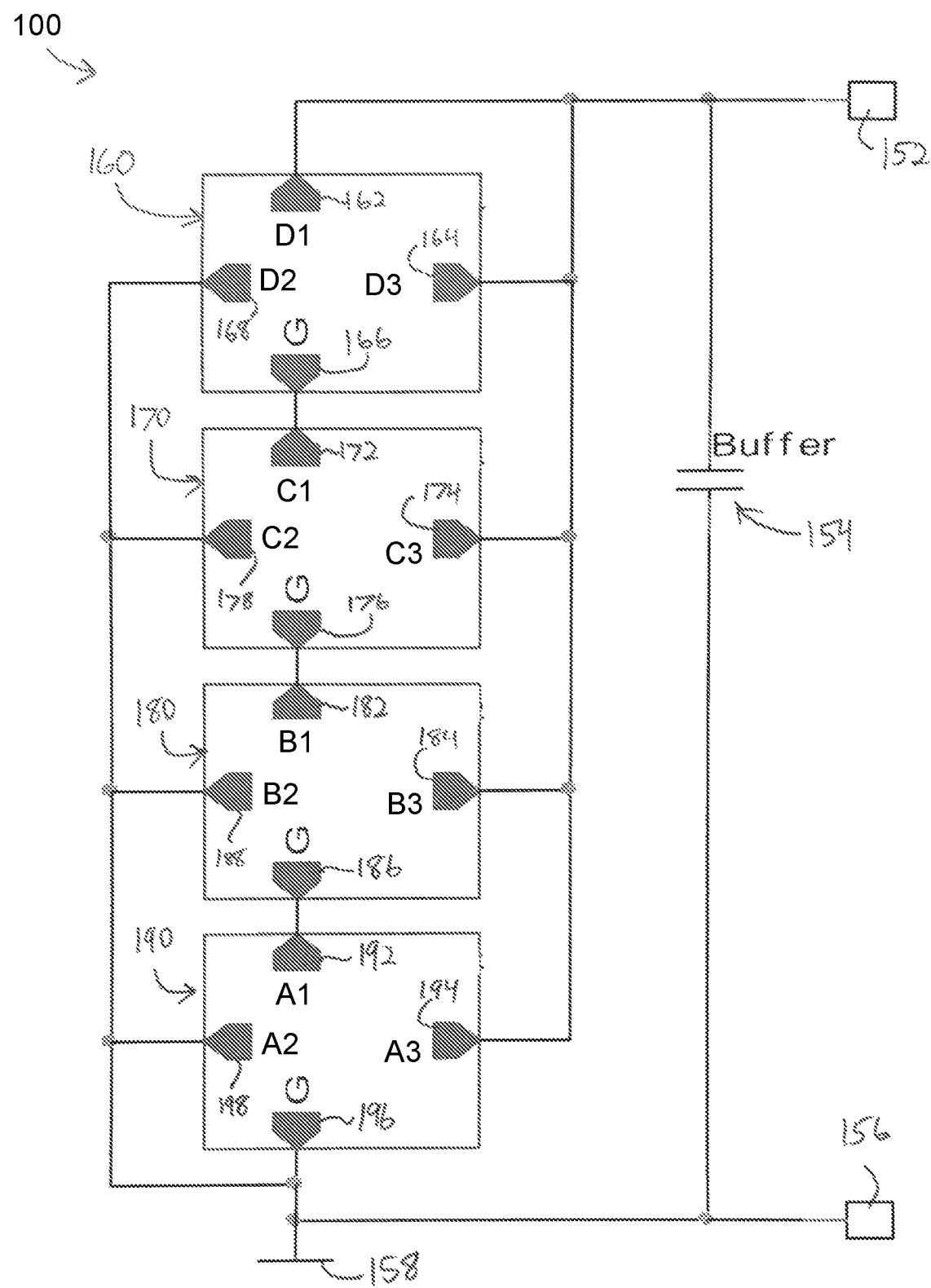
FIG. 7 shows a schematic view of the circuit of FIG. 6 in block form.

FIGS. 6-7 show how an energy supplying circuit 100 may include several modules 160, 170, 180, 190. While four modules 160, 170, 180, 190 are provided in this example, an alternative version of energy supplying circuit 100 may include more or fewer than four modules 160, 170, 180, 190. Each module 160, 170, 180, 190 of energy supplying circuit 100 may be configured and operable similar to module 80 shown in FIGS. 5A-5B and described above.

As shown in FIG. 6, first module 160 includes a beta-voltaic power source 161; a set of switches 163, 165, 167; and a set of ports 162, 164, 166, 168. In this example, switches 165, 167 and ports 162, 168 are not used; though ports 162, 168 may be coupled with an additional module if desired (at which point switches 165, 167 may be used). Second module 170 includes a beta-voltaic power source 171; a set of switches 173, 175, 177; and a set of ports 172, 174, 176, 178. Third module 180 includes a beta-voltaic power source 181; a set of switches 183, 185, 187; and a set of ports 182, 184, 186, 188. Fourth module 190 includes a beta-voltaic power source 191; a set of switches 193, 195, 197; and a set of ports 192, 194, 196, 198. Energy supplying circuit 100 further includes an active port 152, a buffer capacitor 154, and a return port 156. Active port 152 may provide power to one or more active components (e.g., electrical stimulus electrode, sensor, etc.) as described herein. Port 156 may provide a ground return path.

In some versions, circuit 100 may be configured such that each module 160, 170, 180, 190 is operable to supply 0.4 V; such that circuit 100 may be operated to supply power in multiples of 0.4 V. In other words, if each module 160, 170, 180, 190 is operable to supply 0.4 V at 1 µA, then circuit 100 may be selectively operated to supply 0.4 V at 4 µA, 0.8 V at 2 µA, or 1.6 V at 1 µA. The below Table 1 shows the various switch states that may be implemented in circuit 150 to achieve these different states of power supply.

TABLE 1

| Voltage | 0.4 V | 0.8 V | 1.6 V |
|---|---|---|---|
| Max current | 4 µA | 2 µA | 1 µA |
| Configuration | 1S4P | 2S2P | 4S1P |
| Switch | | Switch states | |
| A1 (195) | 0 | 1 | 1 |
| A2 (197) | 1 | 0 | 0 |
| A3 (193) | 1 | 0 | 0 |
| B1 (185) | 0 | 0 | 1 |
| B2 (187) | 1 | 1 | 0 |
| B3 (183) | 1 | 1 | 0 |
| C1 (175) | 0 | 1 | 1 |
| C2 (177) | 1 | 0 | 0 |
| C3 (173) | 1 | 0 | 0 |
| D1 (165) | X | X | X |
| D2 (167) | X | X | X |
| D3 (163) | 1 | 1 | 1 |

Another possibility would be to split one of the modules 160, 170, 180, 190 of this example into 3 smaller modules, with each smaller module supplying ⅓ µA. Such variations may allow the additional provision of 1.2 V at 1.33 µA, at the cost of more switches.

The more modules an energy supplying component or circuit is divided into, the more possible configurations it has. For example, an assembly of 12 modules could be configured to produce either 0.4V at 12 µA, 0.8V at 6 µA, 1.2V at 4 µA, 1.6V at 3 µA, 2.4V at 2 µA or 4.8V at 1 µA when connected as 1S12P, 2S6P, 3S4P, 4S3P, 6S2P or 12S1P, respectively. In some variations, the energy supplying component or circuit could also produce 2.0V at 2 µA, 2.8V at 1 µA, 3.2V at 1 µA, 3.6V at 1 µA, 4.0V at 1 µA or 4.4V at 1 µA by connecting it with some modules unused. However, in some scenarios, there may be no advantage in providing such alternative configurations, as, unlike chemical cells, beta-voltaic cells do not conserve unused output energy for use later on.

Arrangements such as those of circuits 100, 150 may be used to generate the voltage level required for generation of a programmable amplitude stimulus pulse directly from a configurable beta energy supplying component, with no extra charge pump required for voltage conversion. Configuring an energy supply component in accordance with circuits 100, 150 may thus avoid the complexity of a charge pump. Configuring an energy supply component in accordance with circuits 100, 150 may also avoid inefficiency and power losses that may otherwise be associated with charging and discharging the capacitors in a charge pump.

The configuration of an energy supply component that is arranged in accordance with circuits 100, 150 may be changed on the fly by having a microcontroller activate switches 163, 165, 167, 173, 175, 177, 183, 185, 187, 193, 195, 197 in each module 160, 170, 180, 190. Using a microcontroller to activate switches 163, 165, 167, 173, 175, 177, 183, 185, 187, 193, 195, 197 in each module 160, 170, 180, 190 may optimize the configuration in real time (or near-real time) based on the ad hoc needs of the AIMD.

Figure 8A:
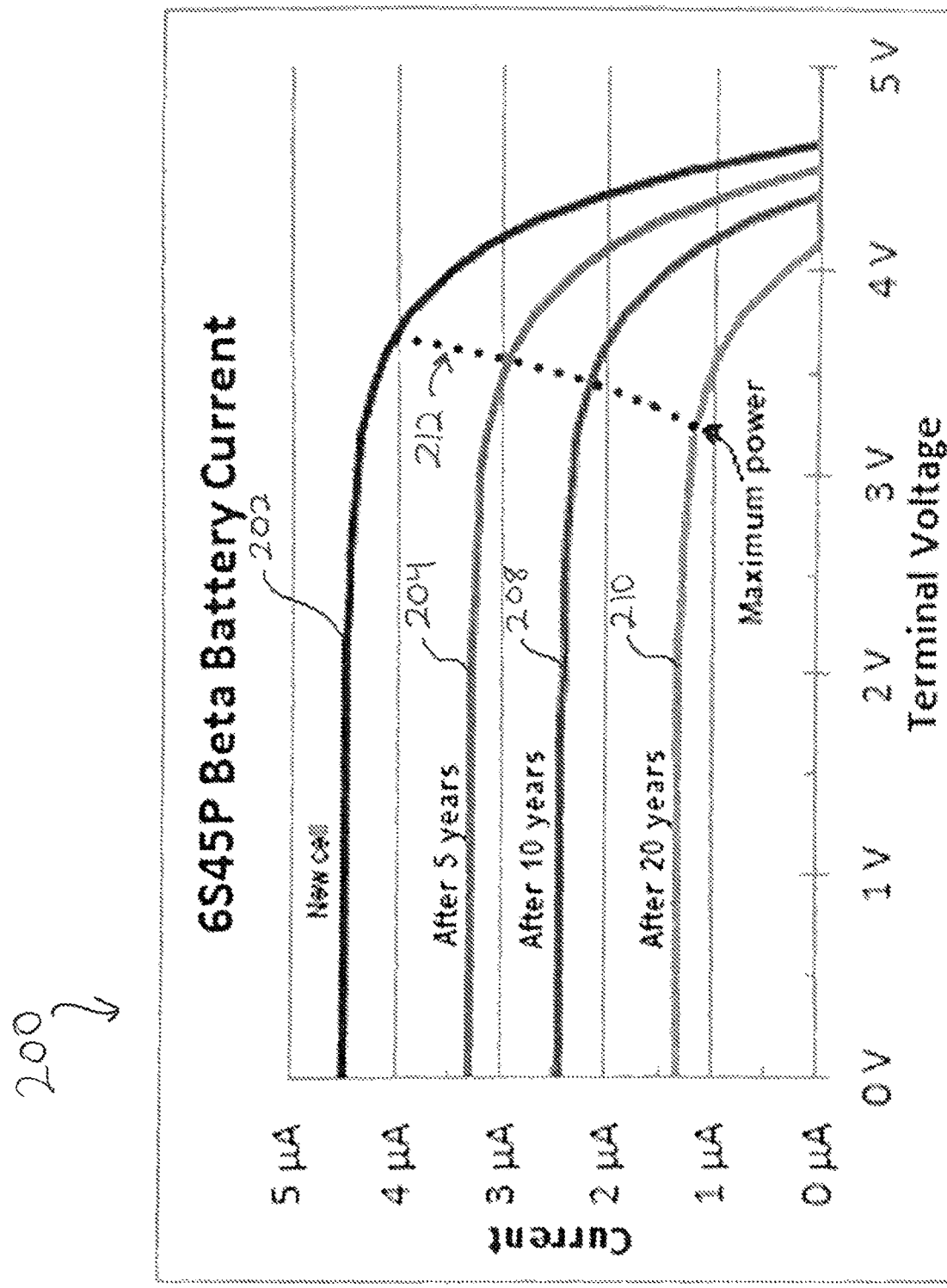
FIG. 8A shows a graph plotting a first set of examples of current and voltage output over different time periods for an energy supplying component.

FIG. 8A shows a graph 200 including plots 202, 204, 208, 210 of examples of output from an energy supplying component. In this example, the energy supplying component is arranged in 6S45P (6 groups in series, each group comprised of 45 cells in parallel for a total of 270 cells), where at the BOL each cell has an open circuit voltage (OCV) of 0.77 V and a short circuit current of 100 nA. In this example, plot 202 is associated with performance of a new cell (0 years), plot 204 is associated with the same cell 5 years later, plot 208 is associated with the same cell 10 years later, and plot 210 is associated with the same cell 20 years later. Line 210 represents the current providing maximum power from the cell as a function of terminal voltage.

Figure 8B:
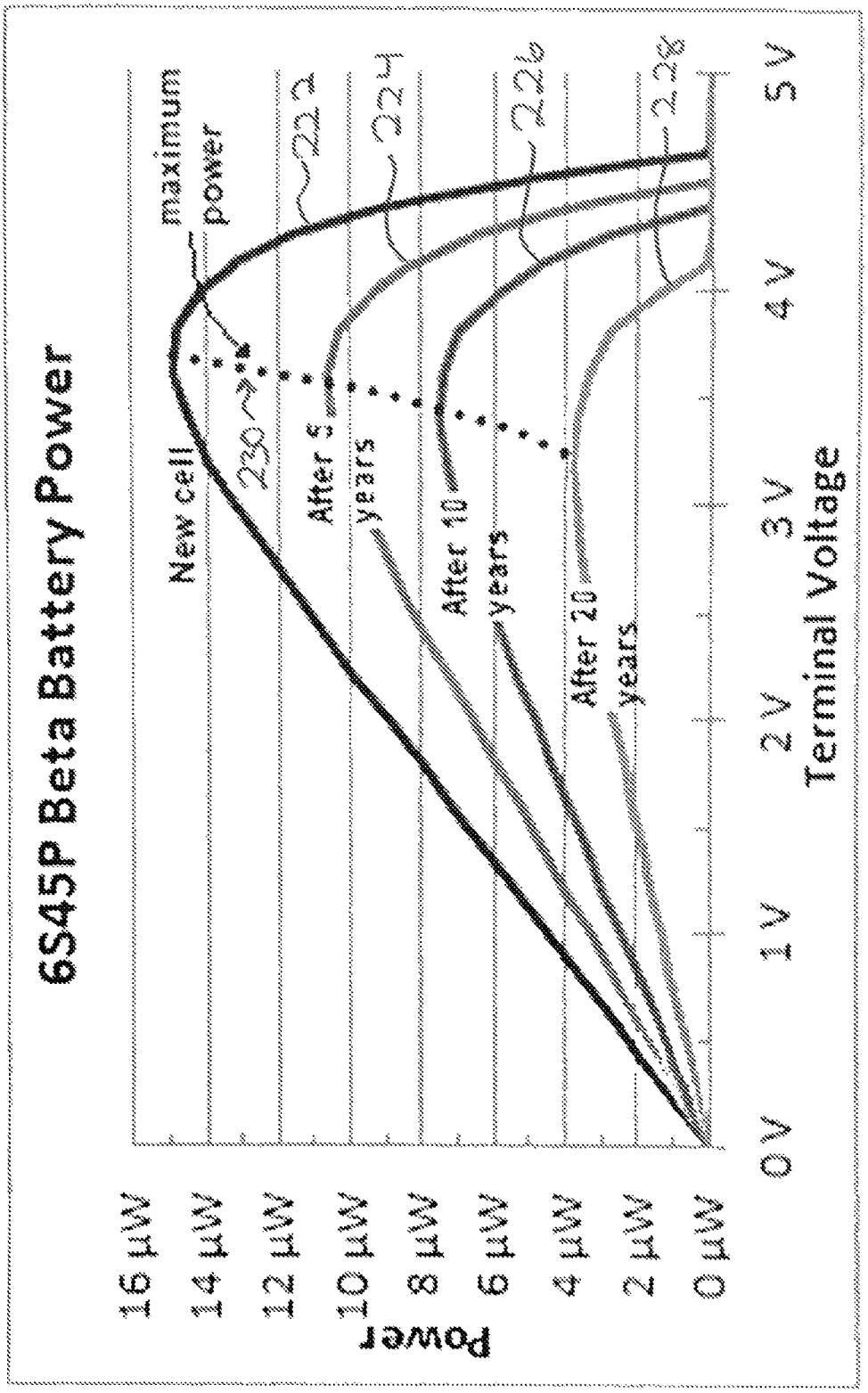
FIG. 8B shows a graph plotting a second set of examples of power and voltage output over different time periods for an energy supplying component.

FIG. 8B shows another graph 220 including plots 222, 224, 226, 228 of examples of output from an energy supplying component. In this example, the energy supplying component is arranged in 6S45P (6 groups in series, each group comprised of 45 cells in parallel for a total of 270 cells), where at the BOL each cell has an open circuit voltage (OCV) of 0.77 V and a short circuit current of 100 nA. In this example, plot 222 is associated with performance of a new cell (0 years), plot 224 is associated with the same cell 5 years later, plot 226 is associated with the same cell 10 years later and plot 228 is associated with the same cell 20 years later. Line 230 represents the maximum power available from the cell as a function of terminal voltage.

Determination of Remaining Service Time:

In a beta-voltaic powered device, it may be unnecessary to use charge counters to determine the amount of charge withdrawn from the energy supplying component, as the energy available from the energy supplying component at any given time will be independent of the energy already used.

However, it is possible that the power output of a beta-voltaic cell may degrade faster than the degradation that would be expected solely from the half-life of the active element of the beta-voltaic cell. For example, leakage of tritium, delamination of the tritium containing metal hydride, or development of defects in the structure of the semiconductor may cause degradation that is faster than the degradation that would otherwise be expected from the radioactive decay of the active element of the beta-voltaic cell. Therefore, in order to be able to provide an estimate of remaining service time, it may be desirable to provide a method of measuring the power available from the energy supplying component at any given time. One possibility is to measure the voltage of the energy supplying component under a known load.

Figure 9:
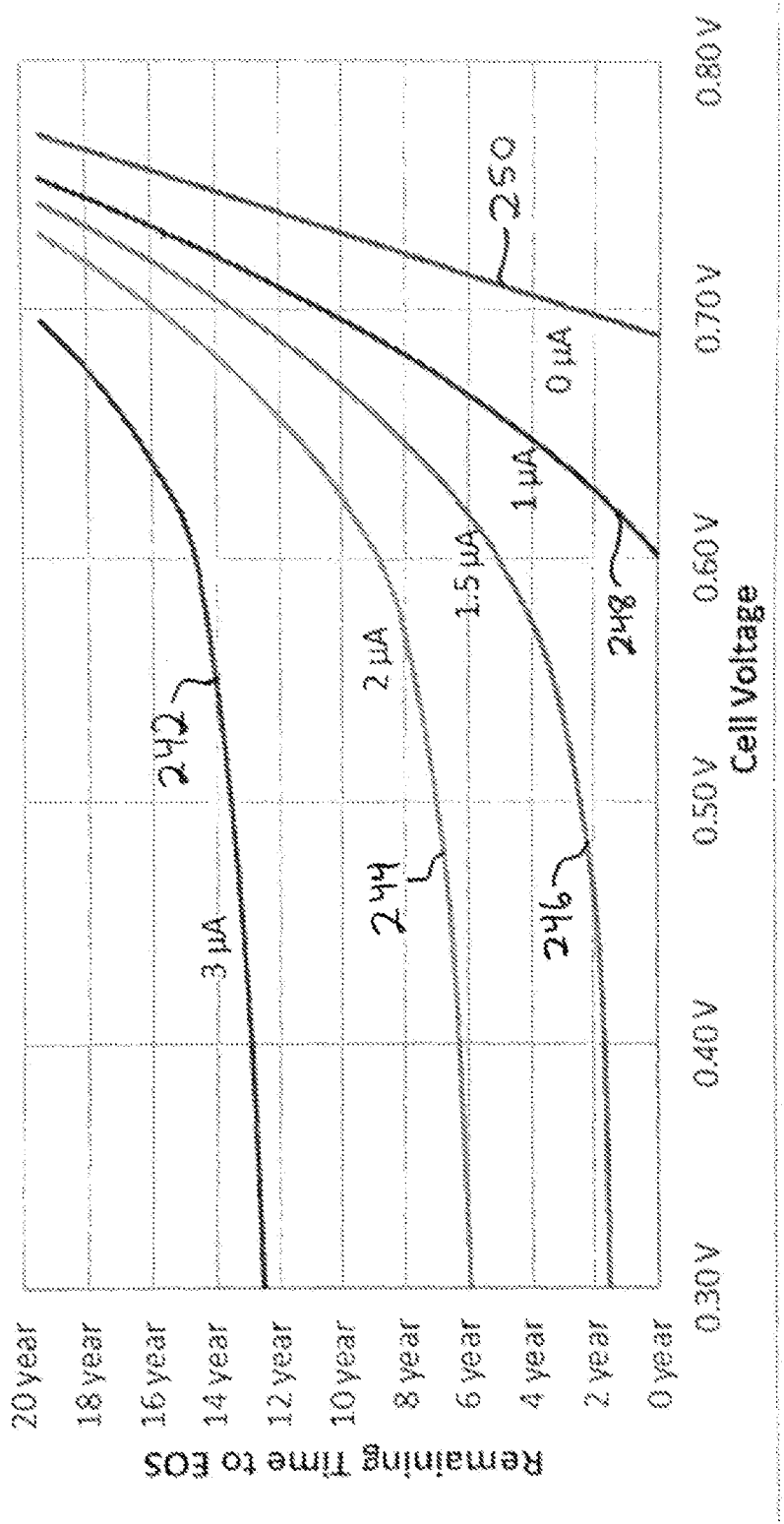
FIG. 9 shows a graph plotting a set of examples of remaining service time as a function of battery voltage as measured under at different loads.

FIG. 9 shows a graph 240 including plots 242, 244, 246, 248, 250 of examples of service time as a function of voltage under a given load, for an examplar battery of 45 cells in parallel, where end of service is defined as when the battery reaches 0.6 V under a 1 µA service load, here at a nominal 16.2 years. In other words, FIG. 9 shows examples of the remaining time that the energy supplying component will be able to deliver at least that service load as a function of its measured terminal voltage under different test loads, neglecting potential degradation from effects other than the expected radioactive decay of tritium. In particular, plot 242 shows service time as a function of voltage under a test load of 3 µA. Plot 244 shows service time as a function of voltage under a test load of 2 µA. Plot 246 shows service time as a function of voltage under a test load of 1.5 µA. Plot 248 shows service time as a function of voltage under a test load of 1 µA. Plot 250 shows service time as a function of voltage under a test load of 0 µA.

Further, an Elective Replacement Indication (ERI) might be defined, where ERI indicates some specified time remaining to End of Service (EOS). Data associated with FIG. 9 is further depicted below in Table 2, which shows several possible values of the interval from ERI to EOS, together with the expected difference between the battery voltage when measured at the time of ERI under a test load to the voltage expected at EOS under the exemplar 1 µA service load.

TABLE 2

| ERI to EOS | Test Load | | |
|---|---|---|---|
| | 0 µA | 1 µA | 1.1 µA |
| 2.0 year | 0.097 V | 0.027 V | 0.013 V |
| 1.5 year | 0.095 V | 0.021 V | 0.006 V |
| 1.0 year | 0.093 V | 0.014 V | N/A |
| 0.5 year | 0.091 V | 0.007 V | N/A |
| 0.0 year | 0.089 V | 0.000 V | N/A |

The method reflected in FIG. 9 may be most easily used if the measurement is made under normal operating conditions, and if the current drawn by the AIMD is known. However, if the AIMD places the energy supplying component under only a light load, the supply voltage may not be very sensitive to the remaining service time. For example, under a 0 µA test load, the supply voltage may change by only about 2 mV in the last 6 months before EOS at 16.2 years. Therefore, the use of a slightly heavier load may be desirable for optimal reporting of remaining service time, although as EOS approaches, the battery may not be able to support more than the service load.

In some versions, an appropriately sized fixed load is switched in periodically (e.g., once per day) for a brief period (e.g., a few milliseconds) to test the resulting supply voltage. In some other versions, the AIMD is powered solely by a buffer capacitor during the period in which the fixed load is switched in. This may ensure that the voltage measurement is not corrupted by varying system loads. In still other versions, each energy supplying module 160, 170, 180, 190 is tested separately for its power availability. As yet another example, the AIMD microcontroller may reconfigure the modules 160, 170, 180, 190 to supplement the output of an underperforming module 160, 170, 180, 190; or to put an underperforming module 160, 170, 180, 190 to use powering a lower power circuit. Some versions of an AIMD may include a small number of excess modules 160, 170, 180, 190; and the microcontroller of the AIMD may switch out an underperforming module 160, 170, 180, 190, replacing the underperforming module 160, 170, 180, 190 with a spare.

The invention claimed is:

1. An energy supplying component (100) comprising:
   (a) a plurality of power sources (161, 171, 181, 191), wherein each power source of the plurality of power sources is configured to output a defined energy level, the plurality of power sources comprising a first beta-voltaic power source (191) and at least one additional beta-voltaic power source (161, 171, 181);
   (b) a plurality of switches (163, 165, 167, 173, 175, 177, 183, 185, 187, 193, 195, 197) configured to reversibly combine two or more power sources of the plurality of power sources for enabling the energy supplying component to supply energy at one or both of a needed voltage or a needed current, the plurality of switches comprising:
   (i) a first switch (193),
   (ii) a second switch (195), and
   (iii) a third switch (197); and
   (c) a plurality of ports (162, 164, 166, 168, 172, 174, 176, 178, 182, 184, 186, 188, 192, 194, 196, 198) the plurality of ports comprising:
   (i) a first port (192), the second switch being interposed between the first power source and the first port,
   (ii) a second port (194), the first switch being interposed between the first power source and the second port,
   (iii) a third port (196), the third port being configured to couple the first power source with ground, and
   (iv) a fourth port (198), the second and third switches being interposed between the first power source and the fourth port,
   wherein the first switch, the second switch, and the third switch are operable to selectively complete a circuit between the first port to the second port, the circuit including one or both of the first power source or the additional power source of the plurality of power sources, and
   the second switch being operable to selectively couple the first power source with the second power source in series, the first and third switches being operable to selectively couple the first power source with the additional power source in parallel.

2. The energy supplying component according to claim 1, wherein at least one switch of the plurality of switches is configured to reversibly combine two or more power sources of the plurality of power sources in a serial configuration.

3. The energy supplying component according to claim 1, wherein at least one switch of the plurality of switches is configured to reversibly combine two or more power sources of the plurality of power sources in a parallel configuration.

4. The energy supplying component according to claim 1, wherein at least one switch of the plurality of switches is configured to reversibly combine a first set of power sources of the plurality of power sources with a second set of power sources of the plurality of power sources in a serial configuration.

5. The energy supplying component according to claim 1, wherein at least one switch of the plurality of switches is configured to reversibly combine a first set of power sources of the plurality of power sources with a second set of power sources of the plurality of power sources in a parallel configuration.

6. The energy supplying component according to claim 1, the first beta-voltaic power source including a tritium-based power source.

7. The energy supplying component according to claim 1, further comprising a buffer capacitor (154), the buffer capacitor being configured to be charged by the two or more power sources of the plurality of power sources reversibly combined by the at least one switch.

8. An apparatus comprising:
   an active implantable medical device (AIMD), the AIMD including one or more of a pacemaker, a defibrillator, an intra-cardiac stimulation device, an implantable loop recorder, an implantable sensor, or a neuro stimulator; and the energy supplying component according to claim 1, the energy supplying component being operable to supply energy to the AIMD.

9. An energy supplying component (100) comprising:
(a) a plurality of power sources (161, 171, 181, 191), wherein each power source of the plurality of power sources is configured to output a defined energy level, the plurality of power sources comprising a first power source (191) and at least one additional power source (161, 171, 181);
(b) a plurality of switches (163, 165, 167, 173, 175, 177, 183, 185, 187, 193, 195, 197) configured to reversibly combine two or more power sources of the plurality of power sources for enabling the energy supplying component to supply energy at one or both of a needed voltage or a needed current, the plurality of switches comprising:
   (i) A first switch (193),
   (ii) a second switch (195), and
   (iii) a third switch (197); and
(c) a plurality of ports (162, 164, 166, 168, 172, 174, 176, 178, 182, 184, 186, 188, 192, 194, 196, 198) the plurality of ports comprising:
   (i) a first port (192), the second switch being interposed between the first power source and the first port,
   (ii) a second port (194), the first switch being interposed between the first power source and the second port,
   (iii) a third port (196), the third port being configured to couple the first power source with ground, and
   (iv) a fourth port (198), the second and third switches being interposed between the first power source and the fourth port; the plurality of switches further comprising:
   (i) a fourth switch (183),
   (ii) a fifth switch (185), and
   (iii) a sixth switch (187); and the plurality of ports further comprising:
   (i) a fifth port (182), the fifth switch being interposed between the additional power source and the fifth port,
   (ii) a sixth port (184), the fourth switch being interposed between the additional power source and the sixth port,
   (iii) a seventh port (186), the seventh port being configured to couple the additional power source with the first port, and
   (iv) an eighth port (188), the fifth and sixth switches being interposed between the additional power source and the eighth port.

* * * * *